United States Patent [19]
Lenihan et al.

[11] Patent Number: 5,683,382
[45] Date of Patent: Nov. 4, 1997

[54] MICROWAVE ANTENNA CATHETER

[75] Inventors: Timothy J. Lenihan, Reading, Pa.; Kenneth L. Carr, Harvard; Mark Guetersloh, Bedford, both of Mass.

[73] Assignees: Arrow International Investment Corp., Reading, Pa.; Microwave Medical Systems, Acton, Mass.

[21] Appl. No.: 440,716

[22] Filed: May 15, 1995

[51] Int. Cl.$^6$ .................................................. A61N 5/02
[52] U.S. Cl. ............................ 606/33; 607/101; 607/156
[58] Field of Search .......................... 606/33; 607/101, 607/102, 154, 156, 113; 29/825, 828

[56] References Cited

U.S. PATENT DOCUMENTS

| | | |
|---|---|---|
| 4,038,519 | 7/1977 | Fomcras . |
| 4,154,246 | 5/1979 | LeVeen . |
| 4,156,429 | 5/1979 | Amundson . |
| 4,202,336 | 5/1980 | van Gerven . |
| 4,346,715 | 8/1982 | Gammell . |
| 4,346,716 | 8/1982 | Carr . |
| 4,448,198 | 5/1984 | Turner . |
| 4,557,272 | 12/1985 | Carr . |
| 4,583,556 | 4/1986 | Hines et al. . |
| 4,641,649 | 2/1987 | Walinsky et al. . |
| 4,643,186 | 2/1987 | Rosen et al. . |
| 4,825,880 | 5/1989 | Stauffer et al. . |
| 4,924,863 | 5/1990 | Sterzer . |
| 4,945,912 | 8/1990 | Langberg . |
| 4,979,510 | 12/1990 | Franz et al. . |
| 5,150,717 | 9/1992 | Rosen et al. . |
| 5,254,088 | 10/1993 | Lundquist et al. . |
| 5,257,451 | 11/1993 | Edwards et al. . |
| 5,273,535 | 12/1993 | Edwards et al. . |
| 5,275,162 | 1/1994 | Edwards et al. . |
| 5,281,217 | 1/1994 | Edwards et al. . |
| 5,293,869 | 3/1994 | Edwards et al. . |
| 5,370,677 | 12/1994 | Rudie et al. ............................ 607/156 |

FOREIGN PATENT DOCUMENTS

| 2027594 | 2/1980 | United Kingdom . |
|---|---|---|

OTHER PUBLICATIONS

"Production of Reversible and Irreversible Atrio–Ventricular Block by Microwave Energy." Beckman, Wang, et al.

"Percutaneous Ablation of the Atrioventricular Junction With a Helical Microwave Antenna: A Novel Means of Coupling Energy to the Endocardium." Langberg, Chin, et al.

"Microwave Ablation of Ventricular Mycardium: The Effects of Varying Duration on Lesion Volume," Cohen, Coggins, et al.

"Efficacy of Microwave Energy for Ventricular Ablation" Coggins, Cain, et al.

"What is the Radial Temperature Profile Achieved During Microwave Catheter Ablation With a Helical Coil Antenna in Canine Myocardium?" Haines and Whayne.

"Comparison of Thermal Profiles Produced by New Antenna Designs For Microwave Catheter Ablation," Whayne & Haines.

"The Effect of Antenna Design and Microwave Frequency on Tissue Temperature Profiles during Microwave Catheter Ablation in vitro," Whayne, Nath, et al.

"What is the Isotherm and Time Course of Lesion Formation in Microwave versus Radiofrequency Catheter Ablation?" Whayne, Nath, et al.

"Application of Ultrasound Energy for Intracardiac Ablation of Arrhythmias." He, Zimmer, et al.

"Delivery of Radiofrequency Energy to all Four Poles of a Catheter Increases Lesion Size," Mackey, He, et al.

"A New Radiofrequency–Powered, Thermal Balloon Catheter for Ablation of Bypass Tracts Via the Coronary Sinus." Fram, Berns, et al.

(List continued on next page.)

*Primary Examiner*—Lee S. Cohen
*Attorney, Agent, or Firm*—Amster Rothstein Ebenstein

[57] ABSTRACT

A helical antenna, which is matched to the desired microwave frequency of 915 MHz, comprises a helix having a linear length which is in the range of 74 to 112 mm or a non-zero integer multiple thereof, and which delivers microwave energy in an optimal heating pattern with little reflected power.

7 Claims, 4 Drawing Sheets

OTHER PUBLICATIONS

"Microwave Catheter Ablation under the Mitral Annulus: A New Method of Accessory Pathway Ablation?" Wang, Schoen, et al.

"Computer Modelling of Microwave Antenna Designs Using The Finite Element Analysis Method" Whayne & Haines.

"Left Ventricular Thrombus Formation After High Power Microwave Ablation: Implications for Temperature and Power Regulation?" Wang, Haugh, et al.

"Microwave Ablation for Tachycardia" Lin, Beckman, et al.

"Spiraled–Heliz Antenna for Catheter Ablation of Myocardial Tissue Using Microwave Energy" Mirotznik, Bogen & Foster.

"Catheter Ablation of the Atrioventricular Junction Using a Helical Microwave Antenna: A Novel Means of Coupling Energy to the Endocardium." Langberg, Wonnell, et al.

"Evaluation of Microwave and Radio Frequency Catheter Ablation in a Myocardium–Equivalent Phantom Model," Wonnell & Stauffer.

"Physics and Engineering of Transcatheter Cardiac Tissue Ablation" Avitall, Khan, et al.

"Microwave Catheter Ablation of Mvocardium in Vitro" Whayne, Nath, et al.

MICROWAVE ANTENNA CATHETER

FIELD OF THE INVENTION

The invention relates generally to the field of electromagnetic therapy medical equipment. More specifically, it relates to a microwave transmitter device capable of accurately and efficiently delivering microwave-frequency energy to tissue within the human body.

BACKGROUND OF THE INVENTION

In medical technology, it is known to deliver electromagnetic energy, such as direct current or radio-frequency energy to internal tissue by means of a transmitter positioned on or near the tissue, often mounted within or otherwise attached to a catheter. By feeding the catheter through to the region of interest, one can detect, diagnose, and treat certain tissue abnormalities associated with tumors, cardiac arrhythmias, etc. In general, positioning of the energy delivery tip of the catheter is conducted by fluoroscopy, echocardiographic imaging, or monitoring of the localized electrical activity from the antenna tip, such as with electrograms.

Detection of different tissue composition in a region of interest can be conducted not only visually, by the use of a camera probe fed through an inserted catheter, but also by analysis of the tissue response to electrical stimuli, for example, with pacing leads to stimulate cardiac response. Upon detection of abnormal tissue in the region of interest, treatment can be conducted, generally by application of energy to the abnormal tissue in order to ablate or necrose the abnormal tissue by hyperthermia. Hyperthermia is produced by the absorption of energy, for example ultrasound or the above-mentioned electromagnetic energy, by the tissue of interest, and conversion of that energy into heat in the tissue. In many instances, catheter ablation of tissue is the preferred treatment for cardiac arrhythmia.

As the technology has developed, different forms of transmitted energy have been evaluated in terms of appropriateness and effectiveness for particular applications, locations, and tissue types. Direct current, which was first utilized for ablation/necrosis treatment applications, has been largely replaced by alternating current applications for several reasons. The direct current pulses were generally found to be painful to patients, therefore requiring the use of general anesthesia when such would otherwise not be necessary. Moreover, the incidence of formation of explosive gases and shock waves resulting from the application of the direct current has driven medical technicians, scientists, and doctors to seek alternative modes of locally delivering high amounts of energy to tissue in a region of interest.

Radio-frequency A/C energy, requiring the mounting of electrodes on or near the tissue in the region of interest, has been found to be a more controllable and predictable resistive heating means for ablation/necrosis applications, as representatively taught in U.S. Pat. No. 4,945,912 of Langberg. Radio-frequency waves, generally in the range of 500–750 KHz, are applied in modulated pulses to avoid arcing and resultant tissue charring. The target tissue is destroyed through resistive heating when energy is delivered between an electrode placed against the target tissue and a ground plate, usually placed in the back of the patient. The heating is dependent upon good contact and on the quality of the resistive path between the electrode and the ground plate. Radio frequency ablation is effective for certain cardiac arrhythmias, such as Supra Ventricular Tacchycardia (SVT), wherein only a small ablation lesion is required to correct the condition. Radio-frequency heating is, however, resistive heating and encounters impedance increase during use, which decreases the capability of further heating thereby limiting the size of lesions and the depth of penetration.

Finally, microwave energy, which consists of alternating electric energy in the frequency range of 300 MHz to 3 GHz, has been proposed as a more controllable heating means for ablation. At microwave frequencies, energy can radiate from the antenna causing water molecules and other dipoles to vibrate, thereby resulting in frictional heating. Microwave-frequency energy can be delivered without contact and without the impedance rise associated with RF energy. Therefore, the low-impedance conductive heating can achieve greater depth of tissue heating/penetration, as may be needed for larger treatment areas, such as for treatment of Ventricular Tacchycardia (VT).

It has been found that microwave power distribution around a transmitter tip can be absorbed, radiated or reflected. Ideally, an antenna will radiate all of its energy in a uniform pattern with little or no energy absorbed or reflected. The Federal Communications Commission has set aside microwave frequencies for medical applications, including 915, 2450 and 2700 MHz. We have recognized that greater depth of penetration is realized at lower frequencies and that loss of energy in the catheter's coaxial cable is minimized at lower frequencies. Therefore, development efforts have been conducted to devise an ideal catheter-mountable, delivery system for application of microwave energy at the lower microwave frequencies.

Monopole microwave antennas of the type described and illustrated in U.S. Pat. No. 4,641,649 of Walinsky et al., have been developed for both radio-frequency and microwave applications. The monopole antennas, having the single tip through which all of the energy is delivered, tend to deliver energy in highly-localized uniform patterns. In order to obtain the frequency response required for certain ablation applications, however, it would be necessarily for the monopole antenna to be λ/4 in length, which is impractically large for cardiac treatment and many other applications. Moreover, the isothermal heating pattern for a quarter-wave antenna shows that the conductive heating goes back from the antenna in a spherical shape as illustrated in FIG. 2(a) of U.S. Pat. No. 4,583,556 which issued to Hines, et al. The heating pattern is such that the peak temperature, $T_1$, occurs at the point at which the outer conductor is discontinued, and there is virtually no heating at the antenna tip. This pattern consequently requires that the antenna be passed beyond the object to be heated and, since the energy to be folded back is equivalent to the energy in the forward portion, the antenna length approaches λ/2 which, further, makes it impractical.

Helical antennas have been developed to provide high frequency energy distribution via a catheter with a spirally-wound antenna helix. Helical antennas have been described in the aforementioned U.S. Patent No. 4,583,556 of Hines et al. and U.S. Pat. No. 4,825,880 of Stauffer, et al. With reference to the Figures of the Hines Patent, Hines minimizes the severity of the monopole antenna heating pattern shown in FIG. 2(a) by utilizing the helical design. The isothermal heating pattern for the helical antenna, as illustrated in FIG. 2(b), provides a uniform concentration of conductive heating ($T_1$) about the antenna tip, with less radiative heating generated away from the antenna tip, as shown by $T_2$.

Ideally, an antenna will exhibit at least 90% efficiency, with <10% reflection, and will provide a uniform, predictable and controllable radiative pattern of heating from or at the tip of the antenna without energy being folded back proximal the antenna.

It is therefore an objective of this invention to provide an optimized helical antenna for delivering microwave energy to tissue in a region of interest within a body.

It is a further objective of the invention to provide a microwave antenna catheter exhibiting high efficiency and which is not subject to unpredictable heating patterns.

Yet another objective is to provide an optimized helical microwave antenna which is matched to the ideal 915 MHz frequency for microwave ablation and which has dimensions that are practical for cardiac ablation treatment.

SUMMARY OF THE INVENTION

These and other objectives are realized by the present invention wherein a helical antenna, which is matched to the desired microwave frequency of 915 MHz, comprises a helix having a linear length which is in the range of 74 to 112 mm or a non-zero integer multiple thereof, and which delivers microwave energy in an optimal heating pattern with little reflected power.

BRIEF DESCRIPTION OF THE INVENTION

The invention will now be described with greater detail with specific reference to the attached Figures wherein FIG. 1 illustrates a helical antenna in accordance with the present invention.

FIG. 2 illustrates one coil of wire in the helix for the inventive antenna.

FIG. 3 provides a schematic of a graph plotting the return loss of an antenna over a range of frequencies.

FIGS. 4A and 4B provide graphs of the specific absorption rate (SAR) patterns for microwave antennas matched to 915 MHz and operating in the first and the second modes, respectively.

DETAILED DESCRIPTION OF THE PREFERRED EMBODIMENT

Figure 1:
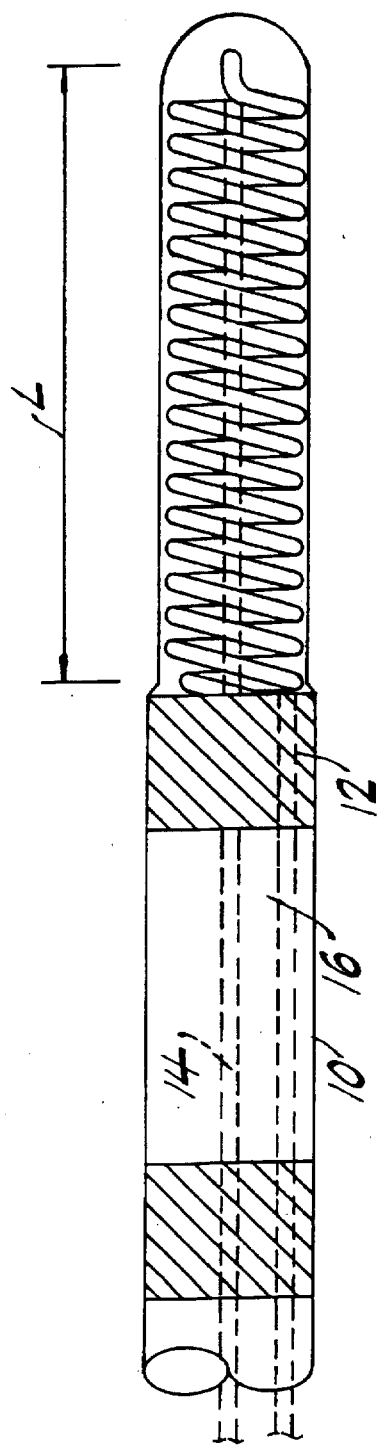

As illustrated in FIG. 1, a helical antenna is provided at the end of coaxial cable 10. The assembly comprises three main components, an outer conductor 12, an inner conductor 14, and dielectric material 16 separating the two conductors. Inner conductor 14 is usually made up of one or more strands of highly conductive metal (e.g., silver-plated copper). The inner conductor is surrounded by dielectric material 16 having a low dielectric constant and low loss tangent (e.g., Teflon). The outer conductor 12 comprises a dense braid, wound coil, foil, or tube of highly conductive metal disposed about the dielectric material 16.

Figure 2:
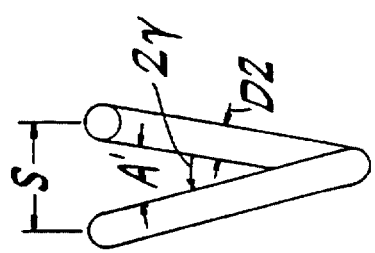

The inner conductor runs through the catheter and extends for antenna span length L (i.e., that part of the radiating element which is exposed beyond the outer conductor and dielectric). The inner conductor is coiled back about diameter D, as measured from the of the conductor, and connects to the outer conductor 12 to form a closed loop. The total length of the wire which is coiled in the helix along L is the linear length, LL. The series of coils of the inner conductor from the end of the outer conductor to the tip comprises the helical antenna of antenna span length L. Reference letter S represents the spacing between turns or coils of the helix, while $2\gamma$ represents the pitch angle of wire at each turn, with $\gamma$ being the deviation from the bisecting line, as further illustrated in FIG. 2. The assembly is further immersed in silicone or similar material encapsulate the assembly.

Figure 3:
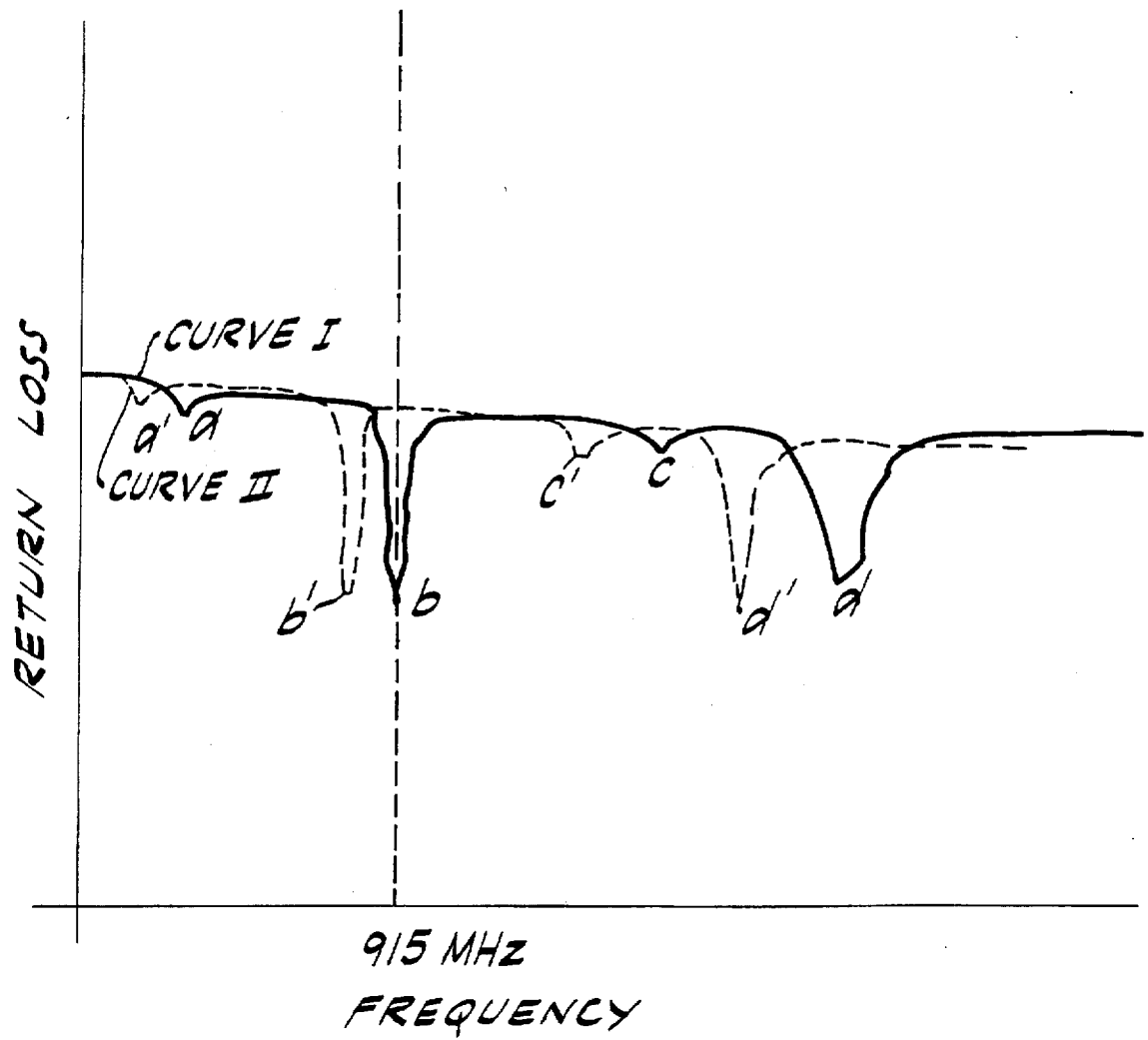

An objective for the inventive helical microwave antenna is to match the antenna to the desired microwave frequency (e.g., 915 MHz) and to minimize the reflected power during antenna operation. FIG. 3 includes schematic graph plotting the return loss (i.e., reflected power) shown in curve I of a microwave antenna across a range of frequencies. The return loss test is performed on a network analyzer and allows one to determine if an antenna is "matched" to the desired operating frequency. In this test, the network analyzer sends out a very small amount of energy to the antenna at a number of different frequencies (e.g., frequencies in the range of 10 MHz to 1 GHz) and records the amount of energy that returns. The recorded energy levels are then plotted on a graph of energy level (in dB) versus frequency (in MHz). The plot starts at 0 dB and the lesser the amount of energy that comes back, the more negative the curve becomes. A well matched antenna would have less than 10% of the energy coming back and would have a large negative number, such as the $-12$ dB value at point B on curve I. An ideal antenna has no returned energy at the operating frequency of the microwave generator.

With reference to FIG. 3, it has been observed that there are discrete points of minimal or decreased energy return loss (hereinafter referred to as "modes") for all helical microwave antennas. The modes, labelled a, b, c and d on curve I in FIG. 3, occur at regular periods along the frequency plot with the first and third modes, a and c, exhibiting a slight decrease in reflected power, while the second and fourth modes, b and d, exhibit a marked decrease in reflected power. Ideally, therefore, an antenna should be matched to operate in one of the modes at the intended frequency (e.g., 915 MHz).

A primary factor influencing the frequency at which an antenna is matched (i.e., where the reflected power is minimized) is the antenna span length L. By increasing the antenna span length, L, while keeping the spacing S and diameter D constant, the return loss plot shifts to the left, with the modes effectively moving from right to left, as illustrated by the points a', b', c' and d' on curve II of FIG. 3. The opposite effect can be realized by decreasing the antenna span length. Further, changing the amount of wire in the antenna, i.e., the linear length LL of the inner conductor wire in the helix from the outer conductor to the tip, by varying the spacing S and/or the diameter D of the helix along a fixed antenna span length L, similarly, affects the frequency of the antenna. Therefore, once the linear length LL had been identified for an antenna matched at 915 MHz, by keeping the amount of wire in the helix, LL, constant, either the spacing S and/or the diameter D of the helix can be changed with the antenna length to arrive at an antenna which operates at the desired frequency.

Antennas were fabricated of antenna lengths aL, bL, cL and dL to operate in each of the modes a, b, c and d to deliver 915 MHz energy with minimal reflected power. A highly conductive metal inner conductor wire was helically wound back about an inner diameter of 1.6764 mm along length L and connected to the outer conductor. In order to fabricate an antenna matched to 915 MHz at each of the identified modes of minimal reflection, the diameter and the spacing between coils of the helix were kept constant and the linear length LL of the wire comprising the helix was varied, as necessarily was the antenna length L. Another way to state variation in the linear length of the wire comprising the helix is to refer to the different number of coils in the helix for each antenna, assuming the spacing and pitch angles are kept constant about a fixed diameter. The linear length can be stated as: $LL = l \times N$, where $l$ is the length of wire in a single turn and N is the number of coils. To determine the value of l, one employs the formula:

$$l = \sqrt{S^2 + C^2},$$

where S is the spacing between coils and C is the circumference of the coils, also depicted as (π), where D is the diameter measured across the coil from one midpoint of a 0.254 mm wire to the other midpoint. Since the spacing between coils is in the order of 0.254 mm, $S^2$ becomes a negligible value, and $l \cong \sqrt{(\delta D)^2}$. At a diameter of 1.9304 mm, l is approximately 6.0645 mm inches per turn.

Once the antennas were fabricated, return loss tests confirmed that each was matched at 915 MHz. Thereafter, the instantaneous heating pattern for each antenna aL, bL, cL and dL was observed. The instantaneous heating pattern of an antenna is determined by calculating the specific absorption rate (SAR) about the antenna. The SAR is calculated using the following formula:

$$SAR = C_p \delta T / \delta t,$$

where $C_p$ is the specific heat of the medium in which the antenna is being tested and $\delta T/\delta t$ is the slope of the temperature versus time curve. When testing microwave antennas for intended use for human cardiac applications, the testing medium of saline most closely approximates the specific heat of blood, which would be the medium in the actual environment for use.

As the antenna is operating in the saline, a temperature probe is positioned at various locations about the antenna and the measured temperature values plotted in a 3-dimensional graph representing the temperature versus time measurements as a function of position. The 3-dimensional graph provides a representation of the instantaneous heating pattern, or the SAR pattern, about the antenna.

The SAR pattern is highly significant in evaluating an antenna for use. If the antenna is not matched at the desired frequency, although it can be caused to operate at that frequency, the resulting SAR pattern will be non-uniform and, effectively, unpredictable. Predictable, smooth and uniform SAR patterns are generated when the antenna is matched to the desired operating frequency (i.e., operating in a mode of minimum reflected power). However, the shape of the instantaneous heating pattern and where the SAR pattern is located with respect to the coaxial cable and the helical antenna differ for the various modes and can alter a determination of usefulness of the antenna for certain applications.

Figure 4A:
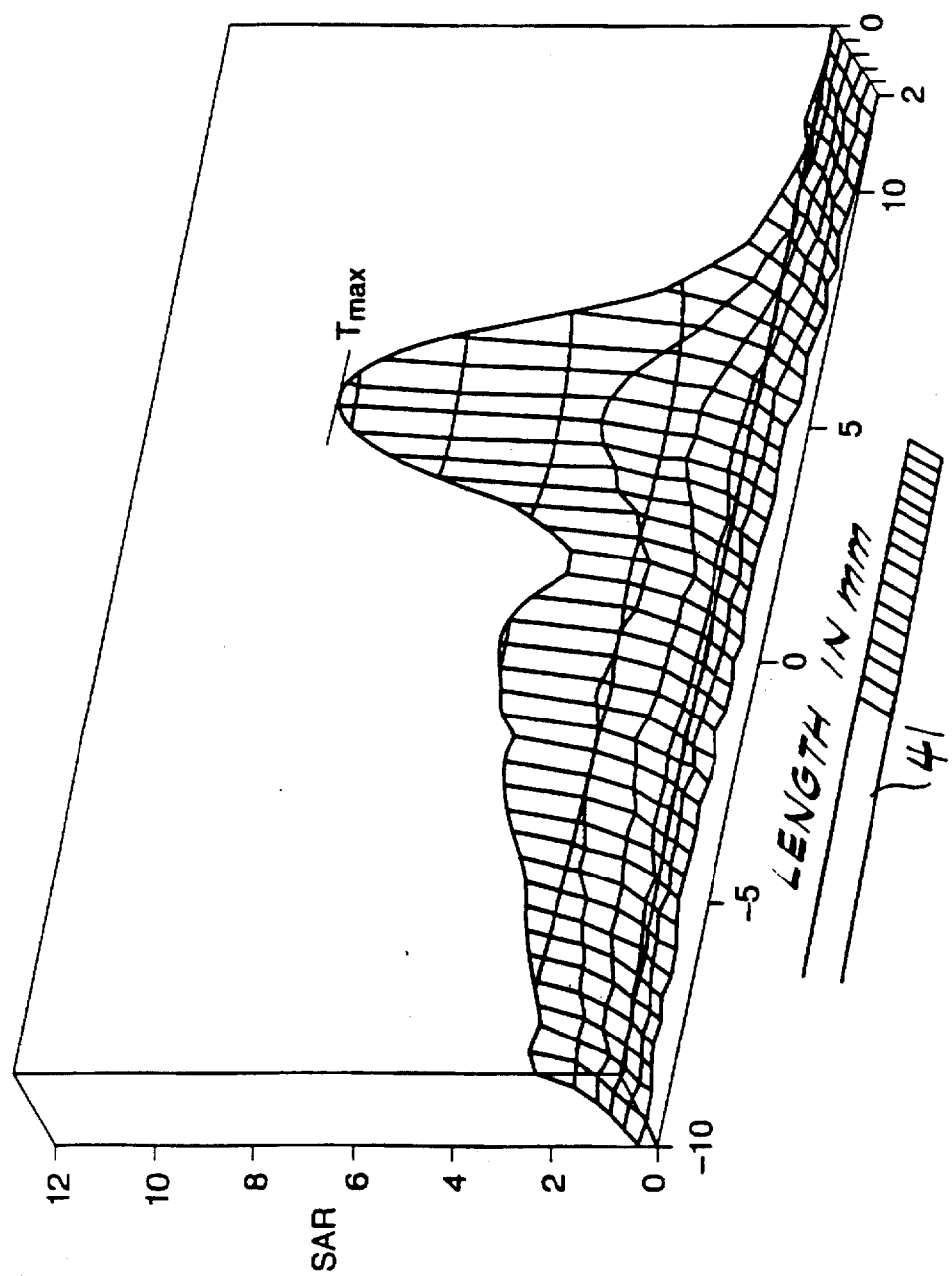
Figure 4B:
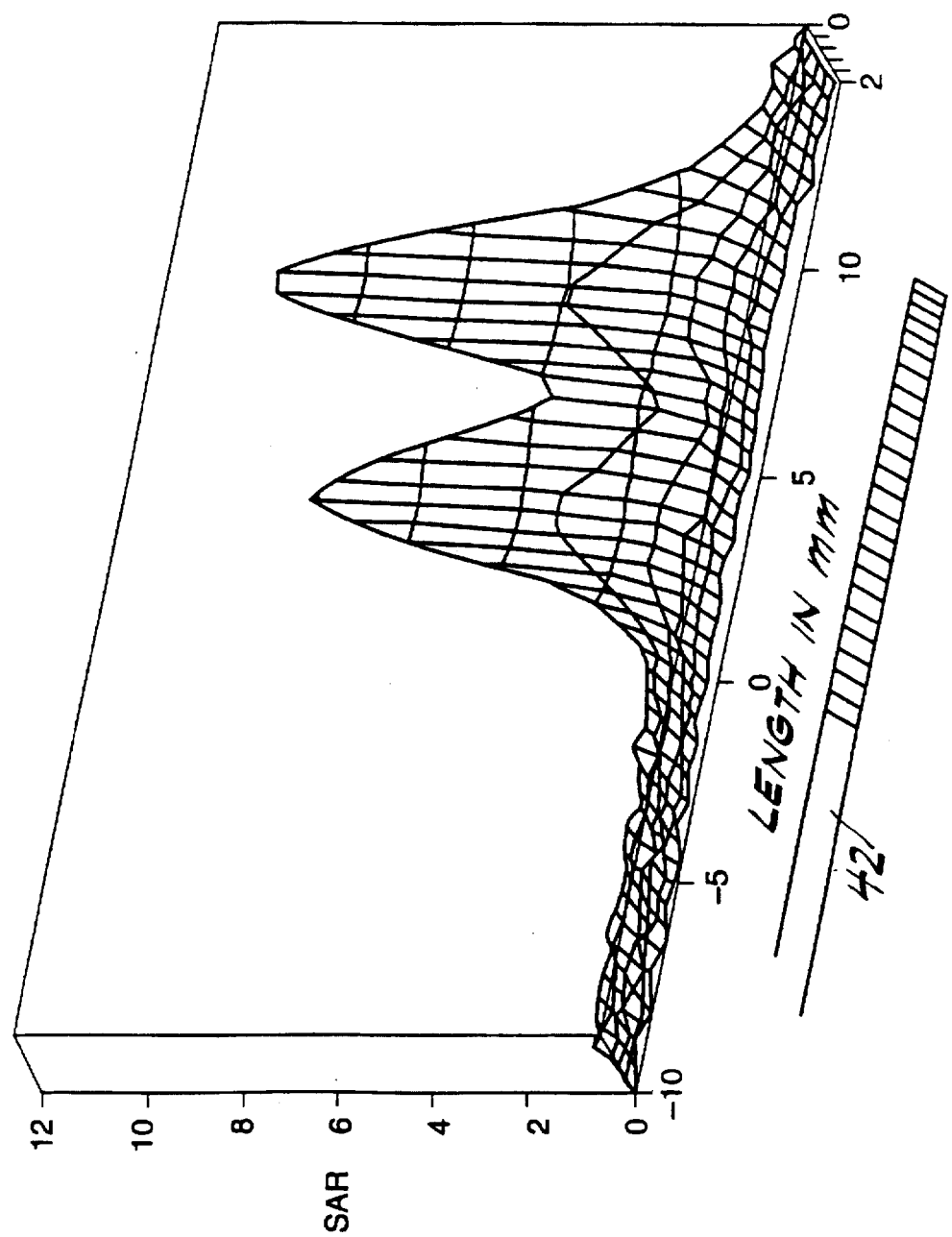

When testing the antennas of lengths aL, bL, cL and dL for operating in the modes a, b, c, and d respectively, it became apparent that the SAR patterns generated for antennas operating in the first and third modes differ from the SAR patterns generated for antennas operating in the second and fourth modes. With reference to FIG. 4A, the span length of the first antenna, aL, as depicted by the schematic antenna 41 beneath the curve, is plotted along the x-axis and extends from the zero (0) point to 5 mm. In FIG. 4B, the span length bL of the second antenna goes from 0 to 10 mm. In each instance, all points to the left of zero represent portions of the coaxial cable.

For the first antenna which was matched to 915 MHz, for operation in the first mode, the antenna length, aL, ranged from approximately 62 mm to 70 mm, or 10.2 coils to 11.6 coils in the helix. The first antenna had the expected efficiency (i.e., reduced return loss), however, the SAR pattern showed radiative heating proximal to the antenna, back over the coaxial cable, representatively illustrated on the negative side of the zero point in FIG. 4A. The SAR pattern with radiative heating proximal the antenna indicates that the aL antenna is not sufficiently controllable for cardiac treatment.

The third antenna, matched to the 915 MHz frequency to operate in the third modes ranged from approximately 124 mm to 136 mm, or 20.5 number of coils to 22.5 number of coils. The third antenna exhibited an instantaneous heating pattern which was very similar to that generated by the first antenna. As with the first antenna, the SAR pattern for the third antenna detected radiative heating proximal the antenna, again raising concerns about the heating control.

As the SAR pattern of FIG. 4A illustrates, some of the radiant instantaneous heating generated by a helical antenna operating in the first mode is folded back over the catheter cable beyond the antenna. The two-hump SAR pattern resulting from operation of the antenna aL, or cL which operates in the third mode, is effectively generated not only over the antenna (e.g., the +5 mm antenna tip at which point $T_{max}$ is encountered) but also beyond the span length, L, of the antenna, and is folded back or reflected over the coaxial cable, 10 (e.g., from 0 to −10 mm). Although fold back may be desirable for some applications, for cardiac treatment it is critical to know that effectively all energy is being delivered over the antenna span length, L. Since, as shown in FIG. 4A, a significant amount of energy in the SAR pattern is emitted in areas which are not over the antenna, non-uniform heating will be encountered over the burn length. Further, it is difficult to definitively ascertain the point at which the fold back region ends, which gives rise to safety concerns.

By contrast, as illustrated in FIG. 4B, with the inventive microwave antenna, schematically positioned under the curve at 42, matched to operate in the second mode for minimized return loss, all of the two-hump SAR pattern is located over the span length, bL, of the antenna, with the heating uniformly distributed along the length of the antenna. Clearly, the second antenna delivers non-ionizing radiation along its length which, by conduction and convection, will fill in the instantaneous temperature dip encountered between the two humps of the SAR pattern to provide uniform heat distribution. The SAR pattern obtained for the second antenna, having linear length of helix wire in the range of approximately 74 mm to 112 mm, or 12.2 to 18.5 coils for the fixed 1.9304 mm diameter, was optimal. In addition, the SAR pattern obtained for the fourth antenna having linear length of helix wire in the range of approximately 148 mm to 224 mm, or 24.4 to 37 coils, also exhibited a uniform SAR pattern with the heating pattern distinctly ending at the proximal end of the antenna.

Therefore, for antennas matched to 915 MHz, optimal antennas which produce favorable instantaneous heating patterns when operating in either the second or the fourth operating mode have been fabricated. Moreover, a relationship between the linear lengths of wire comprising the helixes for second and fourth mode operation matched at 915 MHz has been established, wherein the linear length falls within the range of 74 mm to 112 mm or a non-zero integer multiple thereof.

As previously stated, at a fixed diameter, and fixed pitch angle γ, the relationship between the number of coils and the linear length of the wire comprising the helix varies linearly. However, if the pitch angle γ is changed, it has been ascertained that the same favorable return loss and SAR patterns are obtained provided the linear length of the wire is not changed. Therefore, if the same linear length of wire for the second antenna, bL, is wound about the same diameter, but at a different pitch angle, a different length antenna will be fabricated; but that antenna will still be matched at 915 MHz and operate in the second mode. Similarly, if a wire of linear length which is a non-zero integer multiple of bL is fabricated into a helix, the favorable matching and heating patterns will result.

Although the invention has been described with reference to preferred materials and optimized dimensions and positioning of components, such modification of the system as may occur to one having skill in the art upon a reading of this description will be encompassed in the spirit and scope of the appended claims.

What is claimed is:

1. A helical antenna adapted for coupling to the end of a catheter cable of the type having first and second cable conductors disposed along the length of said cable for delivery of microwave energy along an antenna length, L, comprising:

a first antenna conductor adapted to extend from said end of said catheter cable and having a proximal end adapted to be coupled to said first cable conductor and a distal end; and a second antenna conductor having a proximal end adapted to be coupled to said second cable conductor and a distal end coupled to said distal end of said first antenna conductor, said second antenna conductor comprising a linear length of wire disposed in a number, N, of coils, about a fixed diameter, D, each coil being at a fixed distance, S, from each adjacent coil, the linear length LL of said second antenna conductor being defined by the relation:

$$LL = N(\sqrt{S^2 + (\pi D)^2}),$$

where LL is in the range of 74–112 mm or a non-zero integer multiple thereof.

2. The helical antenna of claim 1 further comprising at least one layer of coating disposed about the length of said antenna.

3. The helical antenna of claim 2 wherein said coating comprises a material having low dielectric and low loss tangent.

4. The helical antenna of claim 3 wherein said coating comprises silicone.

5. The helical antenna of claim 1 wherein said first conductor comprises a plurality of twisted wires.

6. A system adapted to deliver microwave energy to a target area within a region of bodily tissue comprising:

a cable having a distal end adapted to be connected to a microwave energy source and a proximal end for positioning in said bodily tissue, said cable having first and second cable conductors, disposed longitudinally along the length of said cable and terminating at said proximal end of said cable; and a helical antenna disposed at said proximal end of said cable, said helical antenna comprising first and second antenna conductors extending from said proximal end of said cable, said first antenna conductor having a proximal end coupled to said first cable conductor and a distal end, said second antenna conductor having a proximal end coupled to said second cable conductor and a distal end coupled to said distal end of said first antenna conductor, said second antenna conductor comprising a linear length of wire disposed in a number, N, of coils about a fixed diameter, D, each coil being at a fixed distance, S, from each adjacent coil, the linear length, LL of said second antenna conductor being defined by the relation:

$$LL = N(\sqrt{S^2 + (\pi D)^2}),$$

where LL is in the range of 74–112 mm or a non-zero integer multiple thereof.

7. A method for making a helical antenna for delivering microwave energy of a desired frequency only over the length of said antenna, which antenna is disposed at the proximal end of a catheter cable having an outer conductor disposed along the periphery of said cable and an inner conductor disposed within said cable, comprising:

extending a first portion of said inner conductor from the proximal end of said cable to a length L;

coiling a second portion of said inner conductor coupled to said first portion back over said first portion over said length L in a number, N, of coils about a fixed diameter, D, whereby each of said coils is a fixed distance, S, from each adjacent coil and whereby said second portion of said inner conductor has linear length, LL, defined by the relation:

$$LL = N(\sqrt{S^2 + (\pi D)^2}),$$

where LL is in the range of 74–112 mm or a non-zero integer multiple thereof; and coupling said second portion of said inner conductor to said outer conductor.

* * * * *